United States Patent [19]

Carlson et al.

[11] Patent Number: 4,722,839
[45] Date of Patent: Feb. 2, 1988

[54] NOVEL DIOLEFIN PHEROMONE MIMICS AS DISRUPTANTS OF SEXUAL COMMUNICATION IN INSECTS

[75] Inventors: David A. Carlson; John R. McLaughlin, both of Gainesville, Fla.

[73] Assignee: The United States of America as represented by the Secretary of Agriculture, Washington, D.C.

[21] Appl. No.: 704,442

[22] Filed: Feb. 22, 1985

Related U.S. Application Data

[62] Division of Ser. No. 474,996, Mar. 14, 1983, Pat. No. 4,527,000.

[51] Int. Cl.$^4$ ............................................. A01N 25/00
[52] U.S. Cl. ...................................................... 424/84
[58] Field of Search ........................................ 424/84

[56] References Cited

U.S. PATENT DOCUMENTS

| | | | |
|---|---|---|---|
| 2,297,424 | 9/1942 | Maximoff et al. | 585/607 |
| 2,707,196 | 4/1955 | Woods | 585/16 |
| 2,739,995 | 3/1956 | Copenhauer | 585/16 |
| 3,932,616 | 1/1976 | Meresz et al. | 424/84 |
| 3,970,592 | 7/1976 | Ploher | 585/16 |
| 4,016,220 | 4/1977 | Küpper et al. | 424/84 |
| 4,205,066 | 5/1980 | Hennart et al. | 424/84 |
| 4,216,202 | 8/1980 | Klun et al. | 424/84 |
| 4,272,520 | 6/1981 | Kydonieus et al. | 424/84 |

OTHER PUBLICATIONS

Fieser & Fieser, *Advanced Organic Chemistry*, 1961, p. 1419.
Mitchell et al., *Environmental Entomology*, 1975, pp. 577–579.
Tatsaki, *Disruption of Sex Pheromone Communication in Chilo Suppressalis with Pheromone & Analogs*, 1981, pp. 313–325, Inst. of Phys. & Chem. Res. Japan.
Greenblatt et al., *J. Chem. Ecol.*, vol. 2, No. 3, 1976, pp. 285–297.
Rothschild, *Ent, Exp. & Appl.* vol. 17, 1974, pp. 294–302.
Beevor et al., *Bull. Ent. Res.* vol. 67, 1977, pp. 439–447.

*Primary Examiner*—Albert T. Meyers
*Assistant Examiner*—John M. Kilcoyne
*Attorney, Agent, or Firm*—M. Howard Silverstein; David G. McConnell; Raymond C. Von Bodungen

[57] ABSTRACT

Novel diolefin insect pheromone mimics are used to disrupt the sexual communication between insects when applied to an agricultural area in behaviorally effective amounts as follows: (Z)-1,12-heptadecadiene used for *Heliothis zea* Boddie; (Z)-15-methyl-1,9-heptadecadiene used for *Trogoderma variable;* (E)-15-methyl-1,9-heptadecadiene used for *Trogoderma glabrum;* and (Z,Z)-1,12,14-heptadecatriene used for *Amyelois transitella.*

4 Claims, No Drawings

NOVEL DIOLEFIN PHEROMONE MIMICS AS DISRUPTANTS OF SEXUAL COMMUNICATION IN INSECTS

CROSS REFERENCE TO RELATED APPLICATIONS

This is a Division of application Ser. No. 474,996, filed Mar. 14, 1983 now U.S. Pat. No. 4,527,000 which issued July 2, 1985.

BACKGROUND OF THE INVENTION (1) Field of the Invention

This invention relates to new compounds which mimic insect sex pheromone and are used to disrupt sexual communication between the insects.

(2) Description of the Prior Art

Mating communication in moths and other insects can be disrupted by evaporating physiologically large quantities of the major sex pheromone component or components into the air within or over a crop or commodity. This technique is often termed as air permeation and the disruptants are chemicals that have an effect when evaporated into the air at many points surrounding the pheromone emitter.

The disruption of mating communication via air permeation has also been accomplished with non-pheromonal chemicals having structural properties similar to the pheromone components of the target species. The rice stem borer, Chilo suppressalis (Walker), the corn earworm, Heliothis zea (Boddie), and the tobacco budworm, H. virescens (F.) utilize (Z)-11-hexedecenal (HDA) as a major component of the females' sex pheromone. Two groups [E. R. Mitchell, M. Jacobson and A. J. Baumhover, Environ. Entomol. 4, 577–79 (1975) and P. S. Beevor, Dr. R. Hall, B. F. Nesbitt, V. A. Dyck, G. Arida, P. C. Lippold and Oloumi-Sadeghi, Bull. Entomol. Res. 67, 439 (1977).] have shown that (Z)-9-tetradecen-1-ol formate (TDF), a structurally related analog of this aldehyde, is an effective disruptant of mating communication in air permeation trials against these species. Another group [S. Tatsuki, and K. Kanno, pp. 313–325 in E. R. Mitchell, ed., Management of Insect Pests with Semiochemicals: Concepts and Practice. Plenum Press, New York. (1981)] has discovered that an olefin, (Z)-5-hexadecene, will disrupt the mating communication of C. suppressalis. This olefin also inhibits the response of C. suppressalis males to pheromone-releasing females in a trap when it is evaporated from the same locus (trap). Some chemicals act as both communication disruptants and inhibitors of attraction; however, this is not always the case. [See G. H. L. Rothschild, Entomol. Exp. and Appl. 17, 294–302 (1974)].

Greenblatt et al. (1976) showed that (Z)-14-methyl-8-hexadecenal was extremely potent at low treatments, releasing attraction in 50% of male Trogoderma variable at $10^{-8}$ g. This was the most active of the synthesized components of the pheromone blend of this species, and showed less activity against T. glabrum, T. inclusum and T. simplex.

Aldehyde pheromones tend to polymerize when stored in bulk, and present longevity problems in the field due to air oxidation and photosensitivity. Therefore, alternative materials with improved behavioral effects, greater stability and reduced cost are of great interest for use in insect control.

SUMMARY OF THE INVENTION

This invention describes novel compounds for controlling insect pests by interfering with their mating communication. It comprises applying to an agricultural area or vegetation, by dispersion or dispensing a behaviorally effective amount of the following diolefin insect pheromonemimics:
(Z)-1,12-heptadecadiene
(E)-15-methyl-1,9-heptadecadiene
(Z)-15-methyl-1,9-heptadecadiene
(Z,Z)-1,12,14-heptadecatriene

DESCRIPTION OF THE PREFERRED EMBODIMENTS

In general, this invention describes novel compounds which are used to control insect pests by interfering with their mating communication. It comprises applying to an agricultural area, or to vegetation, by means of either dispersion or dispensing, a behaviorally effective amount of the following compounds:
(Z)-1,12-heptadecadiene
(E)-15-methyl-1,9-heptadecadiene
(Z)-15-methyl-1,9-heptadecadiene
(Z,Z)-1,12,14-heptadecatriene This invention operates by disrupting or simulating the natural sex communication of insects in the field. Male insects detect this chemical by their olfactory senses, thereby interrupting chemical signals excreted by females of the same species. The chemical was designed by the inventors to substitute for the natural chemical. It is liberated into the air in very small measured quantities to last as long as possible.

Chemicals of this type are to be dispersed from one or more dispensers or containers deployed in the vicinity of an agricultural field in quantities of 0.1 to 100 mg per container. Dispensers may be attached to the plant, to its foliage, separate stakes or may be dispensed from the air or with ground equipment to land on the plant, foliage or ground. They may also be used indoors for disruption or attraction especially in the dermestid beetles, Trogoderma species. Dispensers are to dispense chemical or chemicals at the rate of 1 microgram to 20 milligram quantities per 24 hour period.

The following are examples of non-oxygenated, doubly or triply unsaturated hydrocarbon analogs (isosteres) of pheromone components that disrupt mating communication of insects:

EXAMPLE 1

Compound to disrupt mating communication of H. zea., (Z)-1,12-heptadecadiene. Synthesis of Diolefin: A suspension was made of 16.3 g (0.046 mol) of methyltriphenylphosphonium bromide (10% excess, Alfa) in 70 ml tetrahydrofuran that was previously dried by boiling over calcium hydride. The mixture was held below 10° C. while n-butyllithium in hexane (0.046 mol, PCR, Gainesville) was added dropwise under $N_2$ atmosphere. The mixture was stirred 1 hour then held below 10° C. during dropwise addition of 10.0 g of (Z)-11-hexedecenal (HDA, 0.042 mol, Chemsampco) in 20 ml dry THF. The mixture was warmed to room temperature overnight with stirring, then partitioned between hexane and water. The hexane layer was washed twice with water, dried and filtered. The crude product was passed through four 45×2 cm columns of silica gel (60–200 mesh, Baker), using hexane as mobile phase for each column. Analyses indicated that most product was eluted in the first 140 ml fraction, using a Varian Model 1400 gas chromatograph (GC) equipped with a 1.8 m×2 mm glass column packed with 3% OV-1 on Chromosorb WAW DMCS (120-140 mesh), held at 110° C. The major peak contained 99.8% of the material seen. It eluted at the equivalent of 16.75 carbons, compared to paraffin standards on the nonpolar column. Evaporation of solvent gave 5.6 g (57% yield) of a clear oil.

The molecular weight was shown to be 236 by chemical ionization GC mass spectrometry with methane used as the carrier and reactant gas, a Finnegan Model 1015 C GCMS with a Varian 1400 GC used as the inlet, and a column as above. Fragments were seen at m/e 235 (M-1, 7%) 236 (M,4%) and 237 (M+1, 3%) that were consistent with the desired diolefin, (Z)-1,12-heptadecadiene, hereafter called DO.

Disruption of Mating Communication in Corn Earworm Via Air Permeation

The DO was evaporated from closed No. 3 Beem embedding capsules, each containing 5 mg material. Each capsule was attached to a wooden stake at a height ca. 15 cm above the plant canopy. A treatment consisted of 16 equally-spaced evaporators within a 100 $m^2$ plot. At the center of each plot was a cone-trap baited with 3 virgin female *H. zea.* The experiment consisted of 6 trapping sites in a peanut field (2 rows of 3 traps each) with 100–180 meters between traps. The treatments were applied to every other site and each time the traps were checked the treatments were moved to the adjacent site.

The traps were inspected 9 times from July 11–23, 1980. Each time the treatment was moved to a previously untreated trap site, the number of males captured by that trap was reduced. Traps at untreated sites captured a mean of 12.4±2.7 (SE) males/trap per trapping interval and traps in DO-permeated areas captured 1.9±0.5 males/trap per trapping interval. These means are statistically different in Duncan's NMR at the 1% level of significance. The greatest reduction relative to the controls was 91.9% and the least reduction 75%.

Comparable reduction in catch of *H. zea* using HDA in the air permeation technique in a Hercon formulation were 90–100% over approximately the same period of field trapping as the present work, while reductions using the formate in Conrel hollow fibers were also 90–100%. Direct comparison of the results with HDA and formate to the 75–92% reductions found here with DO are not appropriate since different formulations were used, but preliminary results are encouraging. Also, it is possible that a blend of DO with small amounts of aldehydes and/or formates may approximate the activity of the best aldehyde blend.

EXAMPLE 2

Synthesis of Diolefins

A suspension was made of 2.5 g (0.0063) of methyltriphenylphosphonium bromide (10% excess, Alfa) in 50 ml tetrahydrofuran freshly distilled from calcium hydride in a septum-equipped 100 ml flask. The mixture was held at 7° C. while 5.6 ml of 1.6M n-butyllithium in hexane (0.0089 mol, Chemical Sample Co.) was added dropwise under $N_2$ atmosphere (Cockerill and Harrison 1977). The light yellow mixture was stirred 1 hour then held below 10° C. during dropwise addition of 1.5 g of (Z)-14-methyl-8-hexadecenal (ZHDA, 0.006 mol) in 3 ml dry hexane. The mixture was stirred overnight at room temperature, then partitioned between hexane and water. The hexane layer was washed twice with water, dried over sodium sulfate and filtered. Solvent removal gave 1.02 g of oil that was eluted from a gravity-fed 1×45 cm column of silica gel (60–200 mesh, Baker), using hexane as mobile phase. Analyses indicated that most of the product was cluted in the first 50 ml fraction, using a Varian Model 2100 gas chromatograph (GC) equipped with a 1.8 m×2 mm glass column packed with 3% OV-1 on Chromosorb WAW DMCS (120–140 mesh), held at 160° C. The major peak contained 87% of the material. It eluted at the equivalent of 17.38 carbons, compared to paraffin standards on the nonpolar column. Evaporation of solvent gave 0.30 g (20% yield) of a clear oil, (Z)-15-methyl-1,9-heptadecadiene (ZTD).

Argentation thin layer chromatography (TLC) was run using REDI-COAT-AG plates of silica gel G with 15% $AgNO_3$ (0.25 mm, Supelco) on the hexane eluent. Only one spot was seen by TLC. Preparative TLC was done on 300 ug of ZTD and the scrapings washed with ether for GC. The $R_1$ was 0.33, compared to 0.66 for paraffin, at 18 CM run height. No evidence for the presence of aldehyde HDA was seen by TLC or GC. The ZTD was 93.5% pure, with impurities at 16.34 (5.4%) and 18.37 (1.1%) carbon equivalents. These were probably diolefinic homologs from, impurities in the starting material, ZHDA.

Chemical ionization GC mass spectrometry (Cl-GC-MS) with methane as carrier and reactant gas was conducted on a Finnegan Model 1015 C GCMS with a Varian 1400 GC used as the inlet, and a column as above. Fragments were seen at m/e 249 (M-1, 7%), 250 (M, 4%) and 251 (M+1, 8%) that were consistent with the desired diolefin, (Z)-14-methyl-1,9-heptadecadiene, hereafter called (trogodermene, ZTD). Analysis calculated for $C_{18}H_{34}$=C, 86.35; H, 13.65.

The (E)-15-methyl-1,9-heptadecadiene (ETD) was synthesized by the same procedures, and obtained in good yield (69%) from 4.9 g of starting material, (E)-14-methyl-8-hexadecenal (EDHA); no aldehyde was present after chromatography on silica gel with hexane.

Bioassays Against 2 Trogoderma Species:

*T. glabrum* (Herbst) males gave a few responses to 0.001 ug to ETD, increasing to 50% responses to 0.01 ug, and good responses at 1 ug in dose-response tests. The authentic (Z)-aldehyde was about one order of magnitude more active than ZTD in comparable tests with *T. variable* (Ballion); good responses were obtained to 0.01 ug of ZTD in preliminary tests. Also, surprisingly good response to 1 ug of ETD mimic in vials was obtained, despite the fact that the natural (E)-aldehyde is not most active against this species. This cross-species activity was unexpected.

Preliminary bioassays were conducted outdoors at the U. of Wisconsin, Madison, Wis. Campus by exposure of authentic pheromone on rubber. Typically, many male beetles were attracted: *T. variable* to authentic (Z)-pheromone, and *T. glabrum* to authentic (E)-pheromone in outdoor tests. Exposure of small amounts (microgram quantities) of (Z)-15-methyl-1,9-heptadecadiene onto septa caused attraction of good numbers of *T. variable* males, while exposure of small amounts of (E)-15-methyl-1,9-heptadecadiene onto septa caused attraction of good numbers of *T. glabrum.*

EXAMPLE 3

Synthesis of Triolefin (TRIENE):

(Z,Z)-1,12,14-heptadecatriene (TRIENE) was synthesized conveniently from Wittig Salt and aldehyde in aqueous dioxidepotassium carbonate heterogeneous medium (Lechat 1982). A mixture of 3.57 g (0.01 mol) of methyl triphenylphosphonium bromide (Alfa Inorganics), 1.7 g (0.14 mol) of potassium carbonate, 10 ml of 1,4-dioxane, 0.15 ml of water and 2.36 g (0.01 mol) of (Z,Z)-11,13-hexadecadienal (AL. Albany International) was prepared in a 100 ml round bottomed flask equipped with a magnetic stirrer, thermometer and reflux condenser. The mixture was heated to reflux at 105°-110° with stirring while aliquots of 15 ul were withdrawn periodically and partitioned between 1 ml of $H_2O$ and 1 ml of hexane. Analysis by gas-liquid chromatography, showed 66, 70 and 99% triolefin and 30%, 26% and 1% starting aldehyde at 1.1 and 2.2 and 17 hr, respectively. More potassium carbonate (1.7 g) was added at 212 hr to drive the reaction to completion. The reaction mixture was cooled and extracted 3 times with 25 ml of hexane, then the organic layer was extracted with water, dried and the solvent removed to leave 1.8 g of yellow oil and a few crystals of triphenylphosphine oxide. The oil was taken up in hexane and passed through a 1×45 cm column of silica gel (60–200 mesh, Baker) with hexane, to yield 1.7 g (73% yield) of clear oil.

Electron impact mass spectra were obtained using a Hewlett-Packard Model 3000 GCMS and a GC inlet fitted with a 25 m×0.2 mm id OV-101 fused silica capillary column in the split mode (99:1) that was temperature programmed from 56° to 188° (upper limit) at 15° per min. The mass spectra showed prominent fragments at m/z 178 (M-56, 3%), 234 (M, 13.5%) and 235 (M+1, 2.5%) for the major peak (Tr 13.4 min, 91%). A smaller peak eluted just before this peak (Tr 13.1 min, 7%) gave an identical mass spectrum. No peak representing the starting aldehyde was seen by GC or by GCMS. An infrared spectrum of the product showed no carbonyl adsorption. Argentation thin layer chromatography using 5% benzene in hexane showed only one spot of $Rf=0.15$.

Bioassay Against *Amylois transitella* (Navel Orangeworm, NOW):

Field tests were conducted in Fresno County, Calif. to investigate NOW mating disruption in commercial almond groves that had previously received pesticide applications. AL and TRIENE were formulated in dispensers of polyvinyl chloride as a plastic laminate sandwich (Hercon Division, Health-Chem Corp., New York, N.Y.). Pheromone used in all tests was 99.5% pure AL (Zoecon Corp., Palo Alto, Calif.).

In a preliminary test, TRIENE was dissolved in hexane (1:2) and dispensed with a 25λ syringe into 1 ml polyethylene Beem capsules. Deployment of Beem caps was as follows: three replications of 9 tree plots, 3 caps per tree, for 72 treatments of 10 mg each. The total amount of TRIENE deployed was 720 mg.

Tests were conducted after the methods reported previously (Landolt et al., 1981), using traps baited with 3, 2 day old, female NOW plus pheromone or mimic in the following manner:
Test 1: Dispenser in trap (0M away)
Test 2: Dispensers near trap (1M away)
Test 3: Dispensers in 8 nearby trees (5–6.4M away)

Plots were monitored with Pherocon 1C traps (Zoecon Corp., Palo Alto, Calif.), each baited with three virgin female NOW contained in a pyramidal fiberglass screen cage (7 by 5 by 4 cm). Trap catches were generally recorded daily, and females were replaced every 3 to 4 days with newly emerged laboratory individuals. Entrapment of males in female-baited traps was used to indicate successful orientation of males to these females. Reductions in numbers of males trapped in treated plots compared with control plots were then considered indicative of disruption of male orientation to trap females.

Test 4: Mating table tests, dispensers (5–6.4M away). Mating success was evaluated with laboratory reared 2-day old virgin female NOW placed in white enamelled pans in plot trees. Dealated moths recovered the following morning were placed in individual cups with paper tops for oviposition. Deposition of variable eggs after 3 days was considered evidence of successful mating as moths ovipositioned on the paper lid the night after recovery, whether mated or not, and variable eggs turned red 1 day later.

Analysis of field treatments: Recovered materials were held at 0° C. after recovery from the field. At the end of the experiment the individual samples were submerged in hexane solvent, and the resulting extract analyzed by GC or concentrated for GC. The GC conditions were: 1.8 m×2 mm id. glass column packed with 3% OV-1 on Chromosorb WDMCS (120–140 mesh) held at 150° C., flame ionization detector.

Release rates of plastic laminate sandwich material recovered from the field were estimated by (Vick et al. 1978 and Landolt et al. 1981) air permeation in a glass container and GC of flask washings, and compared to freshly frozen laboratory-aged dispensers.

PROCEDURES AND RESULTS

Test 1: Dispenser in trap (OM). Formulations were placed directly in female-baited monitoring traps by being pinned to the inside of treatment traps ca. 10 cm above the caged females. A randomized complete block design with three replications within blocks (six traps: three treated, three untreated) was used.

Test 1a: Traps were monitored for 9 nights with 3 replications, for a total of 27 trap nights for each treatment. Table I, (Infra) shows males caught and percent reduction of males caught for AL and TRIENE traps compared to control traps. Disruption of male orientation by AL was 99.5% over 9 days, as only 2 males were caught, 0.7 per trap, while TRIENE traps caught 1 male, a reduction of 99.8%, 0.3 per trap.

TABLE 1

Field Tests of Mating Disruptants for *A. transitella*: (Z,Z)-11,13-hexadecadienal (AL) VS (Z,Z)-1,12,14-heptadecatriene(TRIENE)

| Treatment[a] | Total male capture | x̄ no. males trapped per rep[b] | % Reduction (relative to control) |
|---|---|---|---|
| Control | 351 | 150.3 | — |
| 1a In trap: | | | |
| AL | 2 | 0.7 | 99.5 |
| Triene | 1 | 0.3 | 99.8 |
| 2a Out of trap: | | | |
| AL | 2 | 0.7 | 99.5 |
| Triene | 14[c] | 3.7[c] | 97.5 |

[a]Plastic laminate sandwich
[b]9 nights (3 reps)
[c]5 on 9th night in 1 of 3 traps Test 1b All traps were maintained for 38 nights with 3 replications for a total of 114 trap nights for each treatment and an equal number of controls. Results for the 3 replications were summarized in Table 2, infra, which shows males caught and percent reduction of males caught for AL traps and TRIENE traps compared to control traps. Disruption of male orientation by AL was 99.9% over 38 days, as only 2 males were caught, while TRIENE traps caught 22, a reduction of 98.5% compared to controls, which caught 1155 males. However, the TRIENE-baited traps had excellent activity through day 29, as AL and TRIENE traps caught only 2 males each (99.8% reduction) on 87 trap nights. The TRIENE traps were less effective over the last 8 days (day 30-38), but still gave 91.1 percent reduction during that time.

TABLE 2

Field Test of Mating Disruptants for Male NOW:
(Z,Z)-11,13-hexadecadienal (AL) and
(Z,Z)-1,12,14-heptadecatriene vs. controls

| Nights | Total Male NOW Capture (% Reduction) | | |
|---|---|---|---|
|  | Control | AL | TRIENE |
| Test 1: Dispenser in Trap (0 M) | | | |
| 1-29 | 930 | 2(99.8) | 2(99.8) |
| 30-38 | 225 | 0(100) | 20(91.1) |
| Total | 1155 | 2(99.8) | 22(98.0) |
| Test 2: Dispenser Near Trap (1 M) | | | |
| 1-29 | 930 | 5(99.5) | 36(96.1) |
| 30-38 | 225 | 2(99.1) | 78(65.3) |
| Total | 1155 | 7(99.3) | 114(90.1) |
| Test 3: Dispenser in Nearby Trees (6.4 M) | | | |
| 1-7 | 278 | 1(99.6) | 29(89.6) |
| 8-16 | 538 | 5(98.9) | 227(57.8) |
| Total | 916 | 6(99.3) | 256(72.1) |

| Test 4: Mating Tables, (inhibition test) Dispensers in Nearby Trees (6.4 M) | | |
|---|---|---|
|  | No. females | (% Mated) |
| No. Subjects | 60 | 45 | 45 |
| No. Mated | 18 (30) | 0 (0) | 12 (27) |

Test 2: Dispenser near trap (1M). This test was conducted concurrently with the same experimental design as in test 1, except that 3 dispensers were placed 1 meter equidistant from the trap at the same height in each tree. The same control plots were used for calculating results.

Test 2a: Disruption by AL was 99.5% over 9 days, as only 2 males were caught, 0.7 per trap, while TRIENE traps caught 14 males, a reduction of 97.5%. Five of these males were found in one trap on the last night.

Test 2b: Disruption of male orientation by AL averaged 99.5% over 38 days, as only 7 males were caught, while disruption by TRIENE was 96% over 29 days, and dropped off to 65% over the last 8 days (day 30-38). Good disruption (90%) was obtained over the course of Test 2. (Table 2)

Test 3: Dispensers in nearby trees (6.4M). Comparative disruption of NOW mating was attempted by air permeation with AL and TRIENE. A completely randomized design of 9-tree plots (3 by 3) was used with 3 replications. Trees were 6.4M apart, for a plot area of 0.1 acre. All plots were located in a 32-ha orchard with a minimum interplot distance of 117M. The formulation used was Hercon ® plastic laminate dispensers containing either AL or TRIENE. Four dispensers stapled to lengths of monofilament fishing line were positioned in the canopy of each plot tree, two near the top, one in the center and one at the bottom of each tree, except that none were placed in center trees, which contained monitoring traps. Treated plots received 320 mg of AL per plot (6.9 g/ha) or 608 mg of TRIENE per plot (12 g/ha). Plots were monitored for 38 days with female-baited Pherocon ® traps placed 2M high in the center trees. Results are presented in Table 2 as number of males captured and percent reduction of males captured compared to controls. A total of 916 males were captured in control traps over the first 16 nights of the test. Only 6 males were captured in the AL plots for 99.3% reduction, while 256 males were captured in TRIENE Plots over the same time period for 72.1 reduction. However, 29 males were captured during the first week for 89.6% reduction, and disruption was much poorer during the second week, at only 57% disruption.

Test 4: Inhibition test using Mating tables. Dispensers in nearby trees (6.4M). Mating table tests were replicated 5 times as 12 females were exposed to feral males as controls, while 9 females were exposed in the middle untreated tree of 9 tree AL-treated plots and a like number in TRIENE-treated plots. Thirty percent of females recovered from control and TRIENE plots had been successfully mated, while none were mated in the AL plot. Mating success was not evidently interrupted by the presence of TRIENE in the air released from nearby trees.

We claim:

1. A method for disrupting sexual communication between corn earworms, *Heliothis zea* Boddie, in an agricultural area comprising applying a behaviorally effective amount of insect pheromone mimic (Z)-1,12,-heptadecadiene to the agricultural area to disrupt the sexual communication between the corn earworms.

2. A method for disrupting sexual communication between *Trogoderma variable* in an agricultural area comprising applying a behaviorally effective amount of insect pheromone mimic (Z)-15-methyl-1,9-heptadecadiene to the agricultural area to disrupt the sexual communication between the *Trogoderma variable*.

3. A method for disrupting sexual communication between *Trogoderma glabrum* in an agricultural area comprising applying a behaviorally effective amount of insect pheromone mimic (E)-15-methyl-1,9-heptadecadiene to the agricultural area to disrupt the sexual communication between the *Trogoderma glabrum*.

4. A method for disrupting sexual communication between navel orangeworms, *Amyelois transitella*, in an agricultural area comprising applying a behaviorally effective amount of insect pheromone mimic (Z,Z)-1,12,14-heptadecatriene to the agricultural area to disrupt the sexual communication between the *Amyelois transitella*.

* * * * *